United States Patent
Behnisch et al.

(10) Patent No.: US 8,291,854 B2
(45) Date of Patent: Oct. 23, 2012

(54) DEVICE FOR APPLYING ACTIVE SUBSTANCES TO SURFACES OF MEDICAL IMPLANTS, IN PARTICULAR STENTS

(75) Inventors: Boris Behnisch, Tuebingen (DE); Klaus Epple, Rangendingen (DE); Siegfried Einhellig, Munich (DE)

(73) Assignee: Translumina GmbH, Hechingen (DE)

( * ) Notice: Subject to any disclaimer, the term of this patent is extended or adjusted under 35 U.S.C. 154(b) by 1880 days.

(21) Appl. No.: 11/250,595

(22) Filed: Oct. 14, 2005

(65) Prior Publication Data

US 2006/0124056 A1 Jun. 15, 2006

Related U.S. Application Data

(63) Continuation of application No. PCT/EP2004/003942, filed on Apr. 15, 2004.

(30) Foreign Application Priority Data

Apr. 17, 2003 (DE) .................................. 103 18 803

(51) Int. Cl.
*B05C 5/02* (2006.01)
(52) U.S. Cl. ............. 118/323; 118/58; 118/63; 118/712
(58) Field of Classification Search .................. 118/712, 118/58, 63, 323; 427/2.1, 2.24
See application file for complete search history.

(56) References Cited

U.S. PATENT DOCUMENTS

| | | | |
|---|---|---|---|
| 4,743,252 A | 5/1988 | Martin, Jr. et al. | |
| 5,741,554 A | 4/1998 | Tisone | |
| 6,203,551 B1 | 3/2001 | Wu | |
| 6,395,326 B1 | 5/2002 | Castro et al. | |
| 6,470,302 B1 * | 10/2002 | Cunningham et al. ............ | 703/7 |
| 6,645,547 B1 * | 11/2003 | Shekalim et al. ............ | 427/2.24 |
| 6,743,462 B1 * | 6/2004 | Pacetti ......................... | 427/2.24 |
| 2003/0003221 A1 | 1/2003 | Zhong et al. | |
| 2004/0127987 A1 * | 7/2004 | Evans et al. ................ | 623/11.11 |
| 2006/0073265 A1 | 4/2006 | Teichman et al. | |
| 2006/0124056 A1 | 6/2006 | Behnisch et al. | |

FOREIGN PATENT DOCUMENTS

| | | |
|---|---|---|
| DE | 202 00 220 | 4/2002 |
| DE | 202 00 223 | 4/2002 |
| DE | 103 18 803 | 11/2004 |
| EP | 0 875 218 | 11/1998 |
| EP | 0 950 386 | 10/1999 |
| JP | 1982-211357 | 12/1982 |
| JP | 1993-329423 | * 12/1993 |
| WO | WO-2004/091684 | 10/2004 |
| WO | WO-2005/011561 | 2/2005 |

OTHER PUBLICATIONS

International Search Report for PCT/EP2004/003942, mailed on Aug. 4, 2004, 2 pages.

(Continued)

*Primary Examiner* — Laura Edwards
(74) *Attorney, Agent, or Firm* — Morrison & Foerster LLP (57) ABSTRACT

A device for applying active substances onto surfaces of medical implants, in particular stents, consists of a base station, and of an exchangeable cartridge which can be mounted on the latter. Provided on the cartridge there is a holder for the stents, and a nozzle for spraying the active substance onto the surface of the stent. Provided on the base station there is a drive unit via which the holder and the nozzle are moved relative to one another.

28 Claims, 9 Drawing Sheets

OTHER PUBLICATIONS

Translation of Non-Final Office Action for JP 2006-505121, mailed Apr. 28, 2009.
International Search Report for PCT/EP2007/008587, mailed on Jan. 2, 2008, 2 pages.
Written Opinion of the International Searching Authority for PCT/EP2007/008587, mailed on Jan. 2, 2008, 5 pages.
Restriction Requirement for U.S. Appl. No. 12/419,971, mailed Jul. 22, 2011, 5 pages.
Response to Restriction Requirement for U.S. Appl. No. 12/419,971, filed Aug. 19, 2011, 8 pages.
Office Action for U.S. Appl. No. 12/419,971, mailed Nov. 7, 2011, 9 pages.
Response to Office Action for U.S. Appl. No. 12/419,971, filed Mar. 7, 2012, 11 pages.

* cited by examiner

DEVICE FOR APPLYING ACTIVE SUBSTANCES TO SURFACES OF MEDICAL IMPLANTS, IN PARTICULAR STENTS

RELATED APPLICATION

This is a continuation of copending international patent application PCT/EP 2004/003942 filed an Apr. 15, 2004 and designating the US, which has been published in English as WO 2004/091684 A1 and which claims priority of German patent application No. 103 18 803.7, filed on Apr. 17, 2003. The contents of the above applications are incorporated by reference in their entireties.

BACKGROUND OF THE INVENTION

1. Field of the Invention

The present invention relates to a device for applying active substances to surfaces of medical implants, in particular stents, with a holder for the implants, an arrangement for applying the active substance onto the surface, and a drive unit for moving the holder and the arrangement relative to one another.

2. Related Prior Art

Such a device is known from U.S. Pat. No. 6,395,326 and from DE 202 00 223 U1.

The known devices are provided for coating stents, that is to say vascular prostheses, with medicaments. Such coatings are desirable because, in the first instance, they can improve the biocompatibility of the implants, for example so as to prevent development of thromboses in the case of surfaces coming into contact with blood.

Particularly in the case of stents, it is also known to coat their surfaces with medicaments, for example rapamycin, in order to prevent restenosis through proliferation of the surrounding tissue. Moreover, suitably coated stents are able to deliver medicaments in a targeted manner in situ into the surrounding tissue.

Stents which can be provided with a coating of different active substances have been described by many authors in the prior art; see, for example, DE 202 00 220 U1, EP 0 875 218 A2 or EP 0 950 386 A2.

Other medical implants also often require a suitable surface coating because they have to be biocompatible and their surfaces do not provide for this in the original state. Thus, in the context of the present application, an implant is to be understood as meaning not just prostheses which remain permanently in the patient's body, but also other devices which remain in the body for some time, for example pace makers, heart catheters, any kind of catheter, screws for orthopedic application, long-term catheters, which are used for intravenous feeding, etc., of seriously ill, paralyzed or unconscious patients, and the like more.

In the aforementioned, known devices, the active substance is sprayed via a nozzle onto the outer surface of the stent, where it settles and dries on. To do this, a relative movement between nozzle and stent is needed in the longitudinal direction of the stent, and the stent has to be rotated in the jet of the nozzle, or the nozzle has to be rotated.

It has been found now that the known devices in many respects do not satisfy the latest requirements when using implants in general, in particular stents, and they especially do not satisfy the increasingly necessary or desired flexibility and individual adaptability in the coating. In addition, the known devices are not safe enough in terms of their use by the physician because the latter may come into contact with the active substances, which entails great risks, for example in the case of coatings with adenoviruses. Finally, the known devices are unsatisfactory purely from the point of view of mechanics, hygiene and sterility.

SUMMARY OF THE INVENTION

In view of the above, it is an object of the present invention to make available a novel device which is of the type mentioned at the outset and which avoids these disadvantages.

According to the invention, one object is achieved with a device of the type mentioned at the outset, which comprises a base station and an exchangeable cartridge which can be mounted on the latter, the drive unit being provided on the base station, and the holder and the arrangement being provided on the cartridge.

One object underlying the invention is completely achieved in this way.

The inventors of the present application have in fact found that this two-part design, with a reusable base station and disposable cartridges, affords many advantages. On the one hand, the novel device can be used in the catheter laboratory, so that the physician can decide on the spot as it were, and depending on the particular situation, which active substances and which dose are to be used to coat the implant for the patient concerned.

A further advantage here is that it is possible, during the operation on the patient, to make a decision as to which implant is to be used with which coating. The novel device permits a very rapid coating, so that valuable time is not lost through too long a coating procedure. A coating directly before introduction of the implant has the further advantage that a long storage time of the coated implants is avoided.

Overall, the novel device thus permits a sterile coating procedure directly in the catheter laboratory.

The cartridge is used only once, so that many implants can be coated in succession without extensive cleaning measures, and without the risk of cross-contamination occurring. The cartridge can be designed as a component closed off from the outside, so that the physician comes into contact only with the base station and with the new, sterile cartridge. After coating, the implant is removed and the cartridge is discarded, thus obviating the need to clean the nozzle and holder and avoiding the problems and risks associated with this. This is also particularly advantageous if the coating contains toxic substances.

According to another object the cartridge has a carriage, preferably a spray carriage which is mounted so that it can move in a longitudinal direction and which is in engagement with the drive unit when the cartridge is mounted on the base station.

It is of advantage here that, apart from a fluid connection that may possibly be required, the only connection between base station and cartridge is the connection between spray carriage and drive unit, so that the cartridge can therefore be sealed off effectively from the outside. It is further of advantage that the cartridge is less expensive than it is if it has to be equipped with its own drive unit.

In this connection, it is preferable if the arrangement comprises a nozzle for spraying the active substance onto the surface, the arrangement being preferably provided on the carriage.

It is of advantage here that it is the arrangement or nozzle that is moved, not the implant, so that it is also possible to coat bulky implants, for example stents already crimped onto a catheter, which could be moved only with some effort relative to a stationary nozzle or arrangement.

The nozzle is—according to another object—a first annular nozzle which surrounds the circumference of an implant mounted in the cartridge, it then being further preferred if the first annular nozzle is formed on a first wall of the spray carriage extending transversely with respect to the longitudinal direction, preferably through channels which are distributed symmetrically in a circumferential arrangement and end in a through-hole which surrounds the mounted implant and is provided in the first wall.

It is of advantage here that the number of moved parts can be kept very low. The annular nozzle is only moved in the longitudinal direction with respect to the implant, the circumferential distribution of the sprayed-on active substance is effected via the channels, and it is not necessary for the nozzle to rotate, so that possible damage to the coating is avoided which can arise if the nozzle or even the implant is moved in rotation.

The inventors of the present application were able to show that, with a symmetrical circumferential arrangement of the individual nozzles, it is possible to apply an also radially very uniform coating onto the top surface of the implant.

It is generally preferred if an active substance reservoir in fluid communication with the first annular nozzle is provided on the spray carriage, preferably on the first wall of the latter.

It is of advantage here that the active substance is not delivered by the base station, so that the latter is exposed to less risk of contamination.

A plug connection in fluid communication with the first annular nozzle is preferably provided on the spray carriage, preferably on the first wall of the latter, said plug connection being provided for an exchangeable syringe which holds the active substance or a solution containing the latter.

It is of advantage here that commercially standard syringes can be used as active substance reservoir, whereby it is possible, with one and the same cartridge, to apply different active substances in succession to the implant, and only the syringe has to be changed each time.

In this connection, a limit stop for a piston of the syringe is provided on the base station.

This measure is of advantage from the design point of view because the active substance is conveyed into the nozzle simultaneously via the movement of the spray carriage, and a separate drive is not needed for the syringe piston, the active substance being delivered at the same time as the nozzle is moved along the implant.

According to one development, the cartridge is provided with a second nozzle which, via the base station, is in fluid communication with a reservoir for a drying agent.

It is of advantage here that the cartridge can be used not just for applying the coating, but also for drying the coating, without having to exchange any components. This generally permits rapid coating of the implant, since the drying is accelerated. The drying agent can be compressed air, as is available in the catheter laboratory, delivered via a sterile filter.

According to another object, the second nozzle is also a second annular nozzle which is formed on a first wall of the spray carriage extending transversely with respect to the longitudinal direction, preferably through channels which are distributed symmetrically in a circumferential arrangement and end in a through-hole which surrounds the mounted implant and is provided in the first wall.

It is also of advantage here that the number of moved parts can be kept very low. The annular nozzle is moved only in the longitudinal direction with respect to the implant, the circumferential distribution of the drying agent is effected via the channels, and it is not necessary for the nozzle to rotate.

In another embodiment, seen in the longitudinal direction, the second annular nozzle is arranged behind the first annular nozzle on the first wall.

This measure too affords advantages in terms of time, since the drying takes place immediately after the active substance has been sprayed on. It is not necessary to couple the second annular nozzle to a separate drive or to move it in a second operation past the implant. By this measure, the number of moved parts in the cartridge is further reduced.

In another embodiment, it is further preferred if, between base station and cartridge, at least one sterile filter is provided via which a drying agent can be conveyed into the cartridge when said cartridge is mounted on the base station, the sterile filter preferably being connected to the second nozzle.

It is of advantage here that compressed air available in the catheter laboratory can be used for drying. The sterile filter can be connected to the cartridge and convey sterile air into the inside thereof, and the sterile filter can also be connected to the second nozzle so that the compressed air delivered is used directly for drying. It is also possible to use two sterile filters, of which one is connected directly to the second nozzle and the other to the cartridge interior.

According to another object it is preferred if a transport carriage which can be moved via the drive unit is provided on the base station, said transport carriage being connected to the spray carriage when the cartridge is mounted on the base station, the sterile filter being preferably connected at its first end to the spray carriage and, with the cartridge mounted on the base station, being connected at its second end to the transport carriage.

It is of advantage here that the connection between spray carriage and transport carriage is effected by the sterile filter or sterile filters. Thus, mounting the cartridge on the base station is very simple, and at the same time the attachment of the sterile filters also produces the mechanical connection for driving the spray carriage.

For mechanical reasons and also for reasons relating to sterility, it is preferred if two sterile filters are provided which are connected at their first end to the spray carriage and, with the cartridge mounted on the base station, are connected at their second end to the transport carriage.

Finally, it is also preferred if the cartridge is closed off from the outside, and at least one further sterile filter is provided on the cartridge, via which further sterile filter the cartridge is in fluid communication with its environment.

It is of advantage here that a sterile coating process is possible directly in the catheter laboratory, even if the coating contains toxic substances.

It is generally preferred if the cartridge has, at its end face, a first clamp unit as a holder for the implants, the cartridge preferably being provided with a second clamp unit as a holder for a protective sleeve surrounding the implants, said second clamp unit being able to move relative to the implant in the longitudinal direction in order to remove the protective sleeve from the implant.

It is of advantage here that implants with protective sleeve can be coated without it being necessary to remove the protective sleeve, before fitting the implant, and then reapply the protective sleeve. This ensures, inter alia, good sterility and protects the physician and also the coating during removal of the finished coated implant.

The second clamp unit is preferably formed on the spray carriage, said second clamp unit preferably being formed at a second wall of the spray carriage remote from the end face, and the first and second walls further preferably having a distance from one another, in the longitudinal direction, which is greater than the implant in its longitudinal extent.

These measures are of advantage from the design point of view, because no separate drive is needed for removing the protective sleeve, and the number of moved components is thus further reduced. Moreover, the number of movements needed for coating is reduced, because the protective sleeve is at first gradually drawn off during the movement of the spray carriage and pushed back on again upon reversal of the spray carriage. The distance between first wall and second wall allows the protective sleeve to be drawn off from the implant by a small predetermined distance upon assembly in the cartridge. In this way it is possible, at the end of the coating process, to return the spray carriage past its start position and thus completely push the protective sleeve on, and to use this travel to open the clamp units, so that the implant can be removed from the cartridge without this having to be opened again.

In a further development, the first clamp unit is designed to receive a catheter carrying a stent, and the second clamp unit is designed to receive a protective sleeve fitting over the stent.

In yet another embodiment the base station is provided with a first sensor which indicates when the spray carriage is situated in a start position in which the syringe can be mounted or exchanged, the base station preferably being provided with a second sensor which indicates when the spray carriage is situated in its end position in which the syringe is emptied.

It is of advantage here that the movement patterns are monitored by sensors, which have to be provided just once, and in this way too the cartridge is structurally simple and thus inexpensive.

According to another object, an unlocking arrangement is provided for the first and second clamp units, which unlocking arrangement automatically releases the implant when the spray carriage is moved past its start position, adopted upon mounting of the implant, towards the first end face.

In this way, the implant is released automatically, so that the cartridge no longer has to be opened after coating is completed. This measure thus not only serves to increase the speed of coating, it also protects the coating and the physician.

It is preferred here if the unlocking arrangement for the first clamp unit is arranged between the first end face and the unlocking arrangement for the second clamp arrangement.

This ensures that the protective sleeve is pushed on completely when the implant is released.

It is further preferred if the base station is provided with a third sensor which indicates when the spray carriage is situated in a removal position, in which the first and second clamp units are unlocked, so that the implant can be removed.

It is also of advantage here that the sensor is arranged on the base station.

Overall, the novel device permits rapid, reliable and safe coating of implants of different lengths, and the cartridge to be used just once has only one moved part, namely the spray carriage. The cartridge is thus inexpensive to produce. In addition, the novel device is easy to operate.

It is further of advantage that, in a single linear movement, the content of a syringe can be applied to the surface of the implant and dried. This procedure can, if appropriate, be repeated with a syringe containing a new medicament. The physician can decide on the spot about the nature and dose of the active substance to be incorporated in the coating.

A further object of the invention relates to a cartridge for the novel device. This cartridge is designed as a disposable article and has the features already described in connection with the novel device.

A further object of the invention relates to a base station for the novel device. This base station is re-usable and has the features already described in connection with the novel device.

A further object of the present invention refers to a kit containing a new cartridge and at least one syringe. The syringe through which the active substance is delivered is supplied in the kit together with the cartridge. The syringe too can be designed as a disposable article. In this way, the physician not only has the cartridge to hand, but also the appropriate syringe.

Further advantages and features will become apparent from the following description and from the attached figures.

It will be appreciated that the features explained above, and those still to be explained below, can be used not just in the respectively stated combination, but also in other combinations or in isolation, without departing from the scope of the present invention.

BRIEF DESCRIPTION OF THE DRAWINGS

Embodiments of the invention are set out in more detail in the following description with reference to the figures, in which.

DESCRIPTION OF PREFERRED EMBODIMENTS

Figure 1:
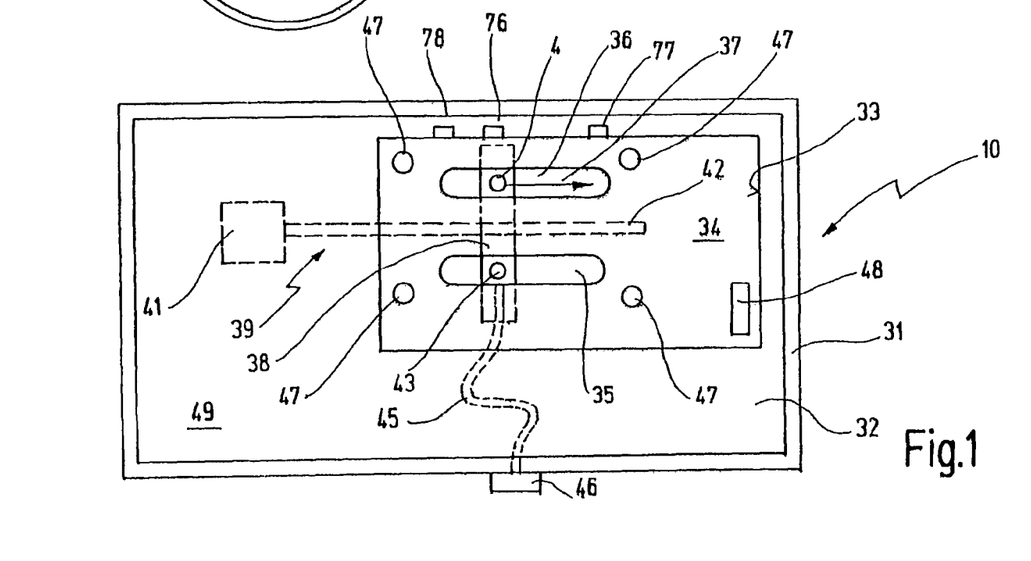
FIG. 1 shows a diagrammatic plan view of the base station of the novel device.
Figure 2:
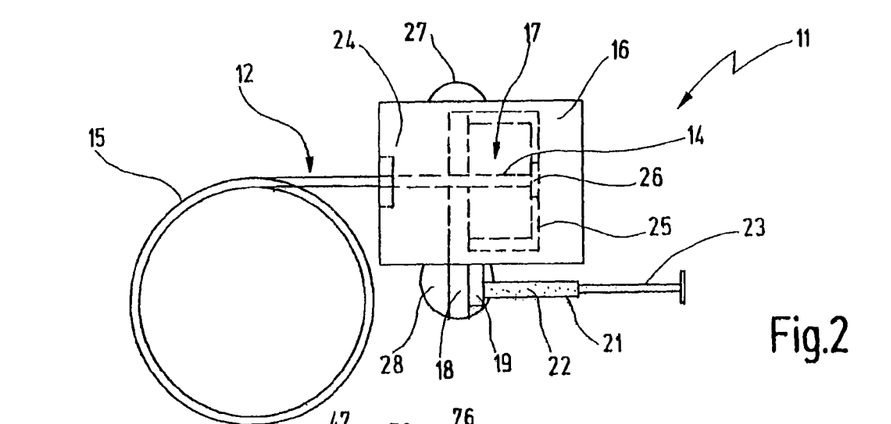
FIG. 2 shows a diagrammatic plan view of the cartridge provided for the base station from FIG. 1.

In FIG. 1, reference numeral 10 designates a base station of the novel device, and FIG. 2 shows a cartridge 11 to be fitted into the base station 10 from FIG. 1. A catheter 12 is fitted into the cartridge 11, said catheter 12 having, at its front end, a stent which is designated by 14 and which is intended to be coated with an active substance via the novel device consisting of base station 10 and cartridge 11. At its other end, the catheter 12 is held in a screw conveyor indicated by 15.

The cartridge 11 has a housing, indicated by 16, which is sealed off in a sterile manner from the outside and, during coating of the stent 14, prevents contamination with the active substance in the laboratory in which the coating is taking place.

The cartridge 11 is supplied in the format shown in FIG. 2, that is to say with the catheter 12 secured on it, and is fitted into the re-usable base station 10 present in the catheter laboratory, for the purpose of coating the stent 14.

A spray carriage 17 is arranged in the cartridge 11 and can move to the left and right in FIG. 2; a syringe 21 sits in a plug connection 19 on the first wall 18 of the spray carriage 17 protruding laterally from the housing 16, into which syringe 21 a medicament indicated by 22 has been drawn which is intended to coat the stent 14. For this purpose, the piston 23 is pushed into the syringe 21, in a manner to be described in greater detail, by which means the medicament 22 passes through channels provided in the first wall 18 to a nozzle (not shown in FIG. 2) which surrounds the stent 14.

In the cartridge 11 there is also a holder for the catheter 12, said holder being indicated by 24, while a second wall 25 of the spray carriage 17 at a distance from the first wall 18 has a holder, indicated by 26, for a protective cap (not shown in FIG. 2) provided on the stent 14.

FIG. 2 also shows two sterile filters 27 and 28 which, in the plan view in FIG. 2, lie under the housing 16 and are in fluid communication, in a manner to be described in more detail, with the first wall 18 of the spray carriage 17.

The cartridge 11 described thus far, with screw conveyor 15, can be fitted into the base station 10 shown in FIG. 1, said base station 10 having a box-shaped bottom part 31 in which a support plate 32 for the screw conveyor 15 is provided. The support plate 32 is provided with a window 33 underneath which a receiving plate 34 for the cartridge 11 can be seen.

Two oblong holes 35, 36 can be seen in the receiving plate 34, these oblong holes 35, 36 extending in a longitudinal direction indicated by an arrow 37.

A transport carriage 38 is mounted displaceably in the longitudinal direction 37 underneath the receiving plate 34. For driving the transport carriage 38, a drive unit 39 is provided which comprises a step motor 41 and an output shaft 42 via which the step motor 41 is in operative connection with the transport carriage 38. Attachments 43, 44 provided on the transport carriage 38 and intended for the sterile filters 28, 27, respectively, can be seen in the oblong holes 35, 36. The attachments 43 and 44 are provided via a flexible tube 45 with a compressed air connection 46, via which compressed air usually provided in a catheter laboratory can be conveyed to the transport carriage 38 and from this through the two sterile filters 27, 28 to the inside of the housing 16 of the cartridge 11. The flexible tube 45 is so dimensioned that it permits displacement of the transport carriage 38 in the longitudinal direction 37.

On the receiving plate 34 there are also four locking elements 47 via which the cartridge 11 can be connected captively but releasably to the receiving plate 34. These locking elements 47 can be locking projections, or alternatively locking apertures into which locking projections latch, and which are provided on the underside (not shown in FIG. 2) of the housing 16 of the cartridge 11.

Finally, at the bottom right of the receiving plate 34, in the window 31, there is a limit stop 48 for the piston 23 of the syringe 21.

As has already been stated, the base station 10, in its intended application, is located in a catheter laboratory where it is connected via its compressed air connection 46 to a compressed air source. This compressed air is used, in a manner to be described in more detail, as a drying agent for a coated stent 14. Moreover, the base station 10 is connected in the normal way to the mains supply or to a suitable battery or suitable generator so as to drive, for example, the step motor 41.

If, for example, in the course of an operation, a stent 14 is now to be coated with a certain medicament 22 and then implanted, a sterile-packed cartridge with screw conveyor 15 and matching stent 14 is taken from storage and is removed from its protective sheath under the sterile conditions in the catheter laboratory. The syringe 21 delivered together with the cartridge 11 is filled with the desired medicament and, if appropriate, with necessary additives, and is then inserted into the plug connection 19.

The cartridge 11 is then placed on the receiving plate 34, so that on the one hand it comes into engagement with the locking elements 47, on which it is held captively, but exchange-ably. At the same time, the sterile filters 27 and 28 come into engagement with the attachments 44 and 43, so that compressed air can pass into the inside of the housing 16 of the cartridge 11. The screw conveyor 15 now lies on the support plate 32 in a receiving area indicated by 49.

The spray carriage 17 is now connected to the transport carriage 38 via the sterile filters 27 and 28, so that it follows the movement of the transport carriage 38 in the longitudinal direction 37. Upon a movement of the spray carriage 17 in the longitudinal direction 37, the syringe 21 is also moved to the right in FIGS. 1 and 2, as a result of which the piston 23 comes into contact with the limit stop 48. If the transport carriage 38 and thus the spray carriage 17 are moved farther to the right, the piston 23 is thereby pressed into the syringe 21, as a result of which the medicament 22 passes, in a manner to be described in more detail, through channels in the first wall 18 and into the inside of the housing 16 where it ensures coating of the stent 14. In other words, as the spray carriage 17 moves to the right, it covers the area of the stent 14 to be coated, while at the same time, through continuous insertion of the piston 23 into the syringe 21, suitable medicament 22 is sprayed onto the surface of the stent 14.

When the coating of the stent 14 is completed and the sprayed-on medicament has been dried by the compressed air, the cartridge 11 with screw conveyor 15 is removed from the base station 10 which, without further cleaning measures, is immediately available for coating of a new stent.

The cartridge 11, however, does not have to be opened, and, instead, the catheter 12 with the now coated stent 14 can be removed immediately, in a manner which will be described below. The remaining, still closed cartridge 11 with sterile filters 27 and 28 and syringe 21 is discarded. In this way, all parts of the coating device consisting of base station 10 and cartridge 11 which come into contact with the medicament 22 are used only once, so that each new stent is as it were delivered with its own new cartridge 11.

In this way it is possible, with the novel device, to coat the stent 14 with a medicament 22, that is to say any desired active substance, under sterile conditions in the catheter laboratory. If so desired, after coating with a first active substance 22, the syringe 21 can be replaced by a new syringe with another active substance, so that the stent 14 can be coated in succession with different active substances or other substances.

Figure 3:
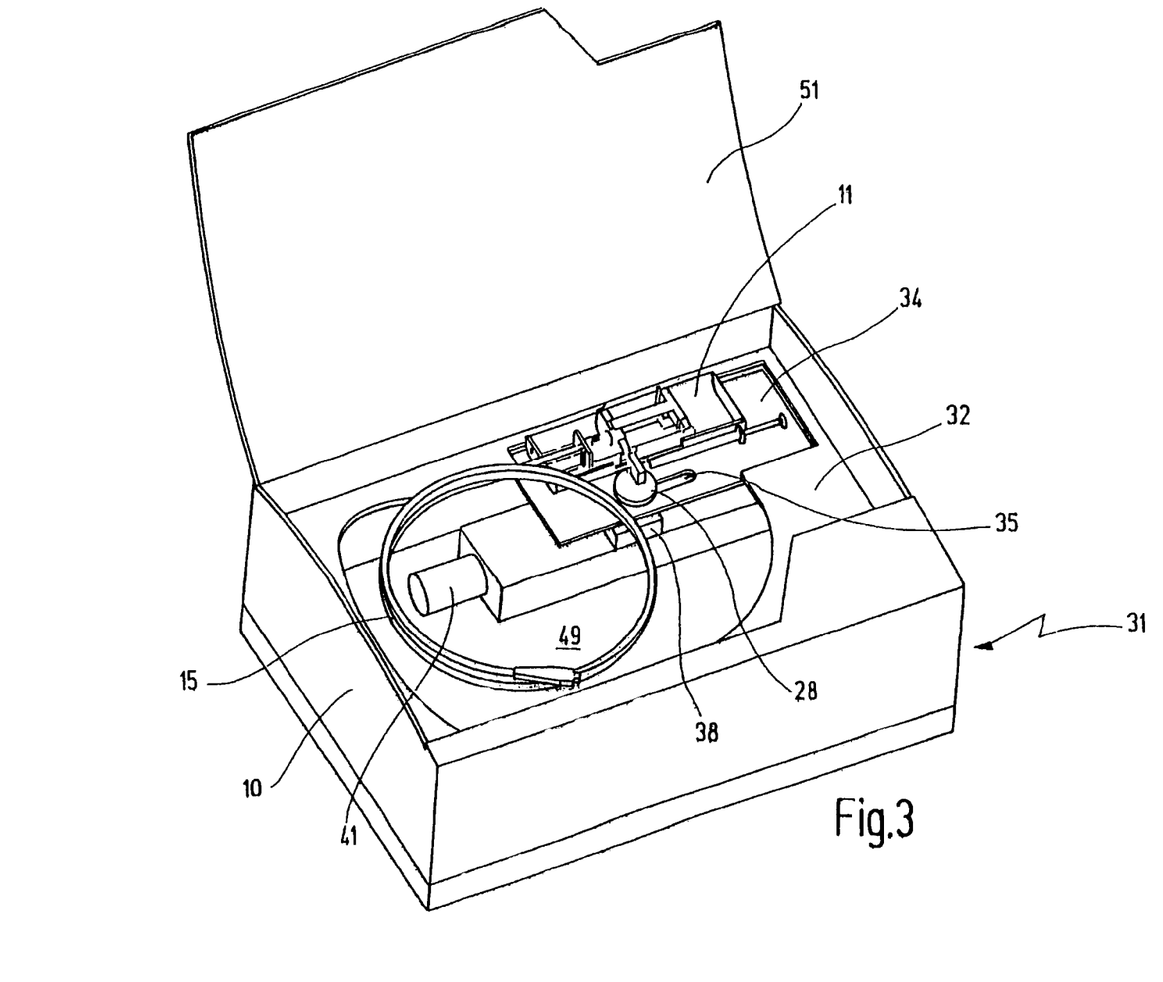
FIG. 3 shows a perspective view of a base station with inserted cartridge.

FIG. 3 is a perspective view of the base station 10 from FIG. 1, with a cartridge 11 from FIG. 2 mounted on it. The support plate 32 is partially cut away so that the transport carriage 38 and the step motor 41 can be seen. Moreover, the figure shows the sterile filter 28 which is provided under the cartridge 11, and below which the oblong hole 35 extends.

The base station 10 is designed as a box whose lower part 31 can be closed by a lid 51. The screw conveyor 15 lies in the receiving area 49 on the support plate 32.

Figure 4:
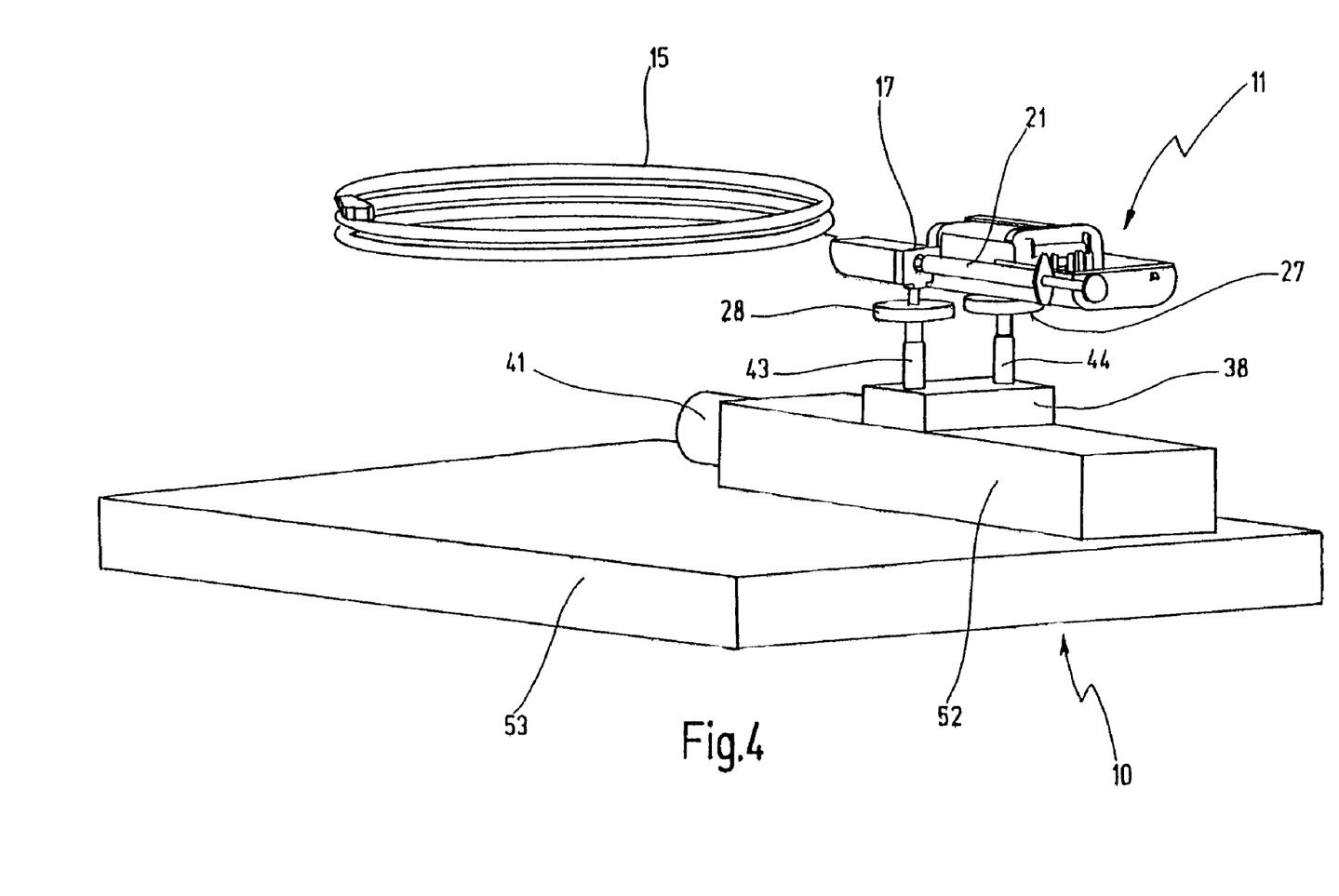
FIG. 4 shows a perspective side view of the connection between base station and cartridge via sterile filters.

FIG. 4 shows a perspective view of the cartridge 11 from FIG. 2 when mounted on the transport carriage 38 from FIG. 1. It can be seen that the transport carriage 38 is connected via the attachments 43 and 44 to the sterile filters 28, 27, which in turn sit on the carriage 17 on which the syringe 21 is also secured, as is indicated at 21.

The transport carriage 38 runs on a guide part 52 which in turn is mounted on a bottom plate 53 of the base station 10.

FIG. 4 also shows that the only connection between base station 10 and cartridge 11 is via the two sterile filters 27, 28, which permit the mechanical connection between spray carriage 17 and transport carriage 38 and also the sterile delivery of compressed air into the inside of the cartridge 11.

Figure 5:
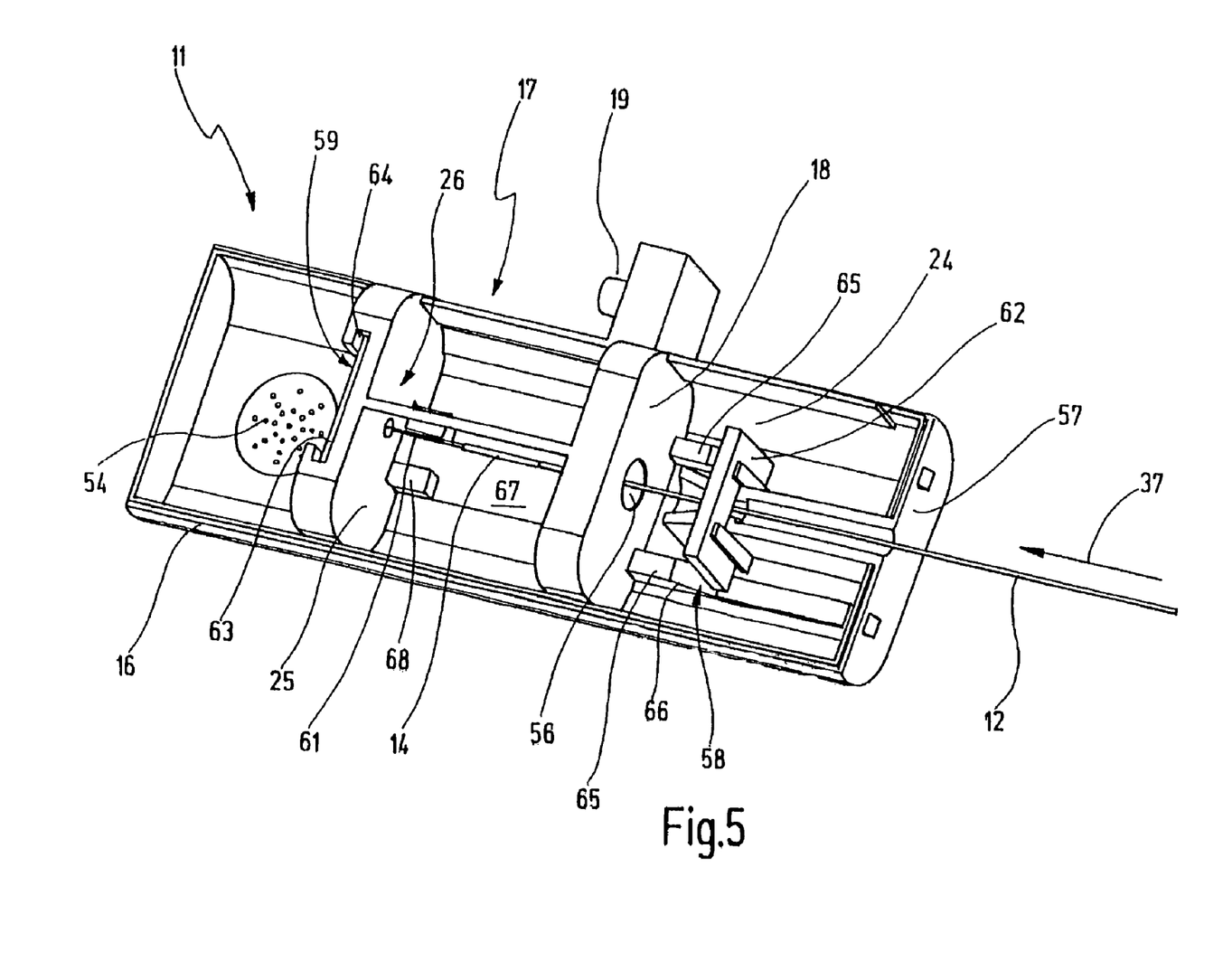
FIG. 5 shows a perspective view of the cartridge from FIGS. 2 to 4 from above, and with the cover removed.

FIG. 5 shows the cartridge 11 from FIG. 2 in a perspective view from above, but with the housing 16 shown without its lid. In the housing 16 there is a further sterile filter 54 via which the cartridge 11 is in fluid communication with its environment. This ensures that medicament 22 sprayed into the cartridge 11 does not get into the environment. The cartridge 11 itself is closed off from the outside, so that, in the catheter laboratory, toxic medicaments can also be used to coat the stent 14.

At its end face 57 on the right in FIG. 5, the cartridge 11 has first holder 24, a first clamp unit 58 which clamps the catheter 12. At the second wall 25 of the spray carriage 17 there is a second clamp unit 59 which clamps a protective sleeve, indicated at 61, for the stent 14. As the spray carriage 17 moves to the left in FIG. 5, the catheter 12 and the stent 14 mounted on it are secured by the first clamp unit 58, while the protective sleeve 61 is drawn off from the stent 14 by the second clamp unit 59, so that the stent 14 can be coated. During the travel of the spray carriage 17, the first wall 18 moves in the longitudinal direction over the stent 14, and in the first wall there is a through-hole 56 in which a nozzle, to be described in more detail, is present which sprays a medicament, delivered via the plug connection 19, onto the surface of the stent 14.

Both the first clamp unit 58 and the second clamp unit 59 comprise a clamp plate 62, 63, respectively, which in each case fits in a transverse slit extending transversely with respect to the longitudinal direction 37 of the catheter 12. Reference number 64 indicates a trans-verse slit of the second clamp unit 59, in which the clamp plate 63 fits.

The clamp plates 62 and 63 are pressed against the bottom of the housing 16 of the cartridge 11, as a result of which they exert a downward clamping action on the catheter 12 and protective sleeve 61.

The spray carriage 17 has longitudinal carriers indicated at 65 which narrow in a wedge shape at their front end 66. When the spray carriage 17 is driven to the right in FIG. 5, the wedge-shaped front ends 66 of the longitudinal carriers 65 pass under the clamp plate 62 and press the latter upwards, so that the catheter is freed from the first clamp unit 58.

In the same way, the inside bottom 67 of the housing 16 is provided with wedges 68 which pass under the clamp plate 63 and push the latter upwards, so that the protective sleeve 61 is freed from the second clamp unit 59, when the spray carriage 17 and with it its second wall 25 are driven far enough to the right in FIG. 5.

The arrangement is designed such that, upon a movement of the spray carriage 17 to the right in FIG. 5, the wedges 68 free the second clamp unit 59 even when the first clamp unit 58 is still in engagement. Only after the protective sleeve 61 has been freed from the second clamp unit 59 do the front ends 66 of the longitudinal carriers 65 pass under the clamp plate 62 so that the catheter 12 too is freed from the first clamp unit and can now be removed from the cartridge, for which purpose it is pulled out counter to the longitudinal direction 37. In other words, this means that, after the end of the coating of the stent 14, the spray carriage 17 moves to the right in FIG. 5 and firstly pushes the protective sleeve 61 back onto the stent 14. The protective sleeve 61 is then freed by loosening the second clamp unit 59. Only now is the first clamp unit 58 freed, again by further movement of the spray carriage 17, so that the catheter with the coated stent 14, onto which the protective sleeve 61 has now once again been pushed completely, can be removed. It is therefore not necessary to open the housing 16 of the cartridge 11 in order to be able to remove the coated stent. Any medicament contamination present in the inside of the cartridge 11 is thus disposed of upon disposal of the cartridge 11.

The fact that, during the travel of the spray carriage 17 to the right in FIG. 5, the second clamp unit 59 is freed first, and only thereafter the first clamp unit 58, ensures that the protective sleeve 61 is pushed back completely onto the stent 14 before the catheter 12 itself is freed.

From what has been said, it will also be evident that the walls 18 and 25 of the spray carriage 17 have, in the longitudinal direction 37, a distance from one another which is greater than the stent 14 in this longitudinal direction 37. In this way, it is possible to initially draw the protective sleeve 61 partially from the stent 14 and then begin coating, as will now be described in detail with reference to FIGS. 6 to 8.

Provided in the first wall 18 of the spray carriage 17 there is a through-hole 56 through which the catheter 12 extends. The first holder 24 is situated to the left of the first wall 18 in FIG. 5, while the second holder 26 is situated on the second wall 25 facing the side of the first wall 18 remote from the first holder 24.

In FIGS. 6 to 8, the cartridge 11 from FIG. 5 is shown in sectioned plan views in different positions of the spray carriage 17. In FIG. 6, the spray carriage 17 is in the start position in which the cartridge 11 can be mounted on the base station 10. For the sake of clarity, FIGS. 6 to 8 do not show the syringe 21 which, via a channel indicated at 71, is in fluid communication with a further channel 72 which leads to a first annular nozzle 73 whose channels end in the through-hole 56 surrounding the catheter 12. Viewed in the longitudinal direction 37, a second annular nozzle 74 is situated on the first wall 18 to the left of the first annular nozzle 73, and its channels likewise end in the through-hole 56. The second annular nozzle 74 is in fluid communication, in a manner to be described in detail below, with a reservoir for a drying agent, and, in the illustrative embodiments shown, the drying agent is compressed air which passes from the compressed air connection 46 on the base station 10 to the sterile filters 27, 28 and from there to the annular nozzle 74.

In the start position shown in FIG. 6, the protective cap 61 is still pushed over the stent 14 (not shown in FIG. 6), and the two annular nozzles 73 and 74 are situated to the left of the protective sleeve 61, viewed in the longitudinal direction 37.

This position of the spray carriage 17 is detected by a first sensor, indicated at 76, which is provided on the base station 10 and records the position of the transport carriage 38. In this start position, a syringe can, as has been stated, be connected to the first wall 18 via the plug connection 19 shown in FIG. 2, in such a way that the medicament 22 passes through the channel 71 and the channel 72 to the annular nozzle 73 when the piston 23 is pushed into the syringe 21.

FIG. 6 also shows the two clamp plates 62 and 63 which clamp the catheter 12 and the protective sleeve 61, respectively.

In FIG. 7, by comparison with FIG. 6, the spray carriage 17 has been driven to the right, so that the protective sleeve 61 has been drawn partially from the now visible stent 14 clamped on the catheter 12. The medicament is now sprayed through the first annular nozzle 73 onto the circumference of the surface of the stent 14, the spray pressure being defined by the piston 23, in contact with the limit stop 48, being pushed into the syringe 21. In other words, only a translation movement of the spray carriage 17 to the right in FIG. 7 is needed in order both to dispense the active substance onto the surface of the stent 14 through the first annular nozzle 73 and also to drive the first annular nozzle 73 along the stent 14. At the same time as the first annular nozzle 73 is moved, the protective sleeve 61 is drawn further from the stent 14.

Figure 7:
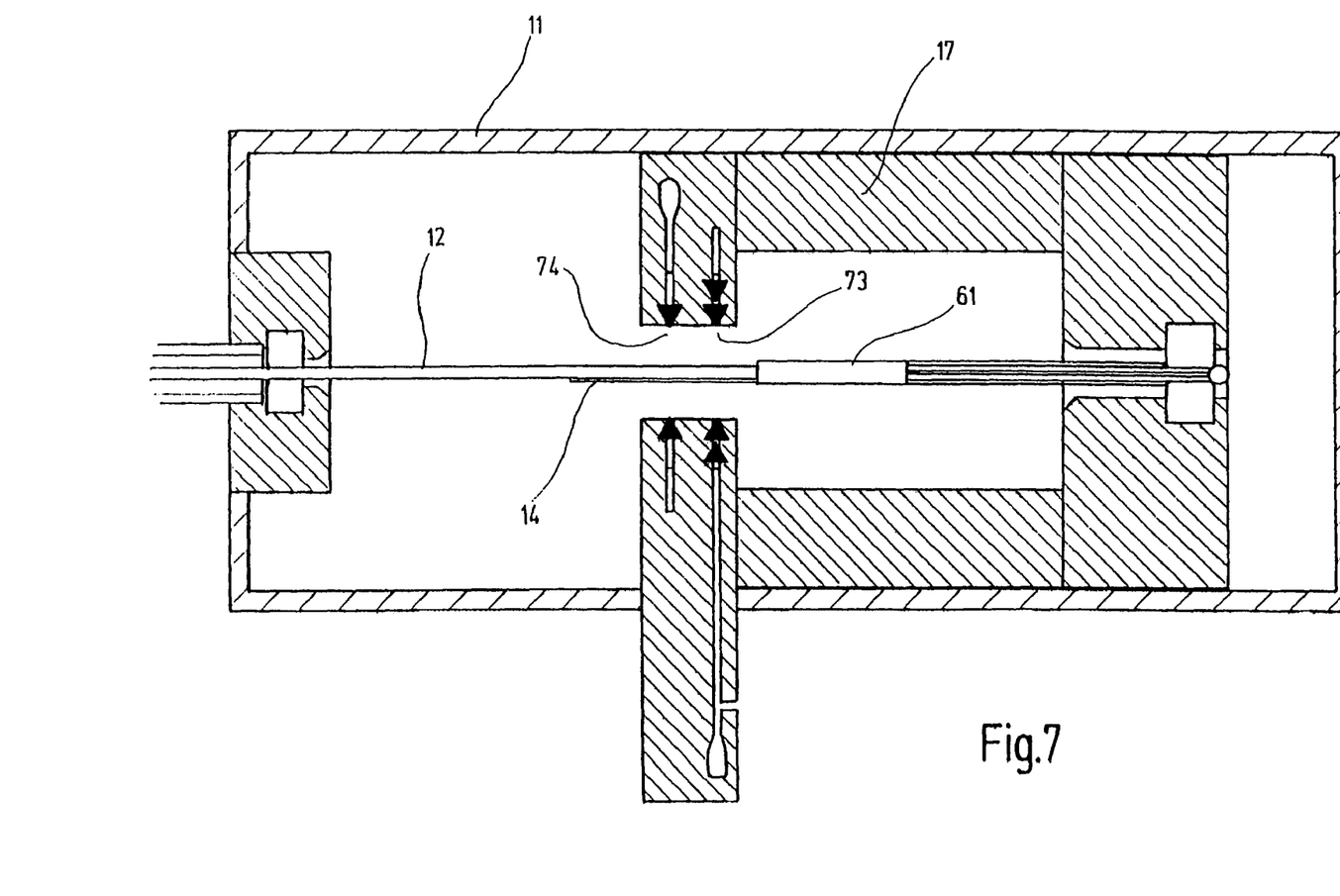
FIG. 7 shows a view as in FIG. 6, the spray carriage being in the coating position.

Since the second annular nozzle 74 is arranged behind the first annular nozzle 73 in the longitudinal direction 37, the sprayed-on medicament is dried, directly after spraying, by the drying agent emerging from the annular nozzle 74, that is to say compressed air that has been filtered to be substantially sterile.

Figure 8:
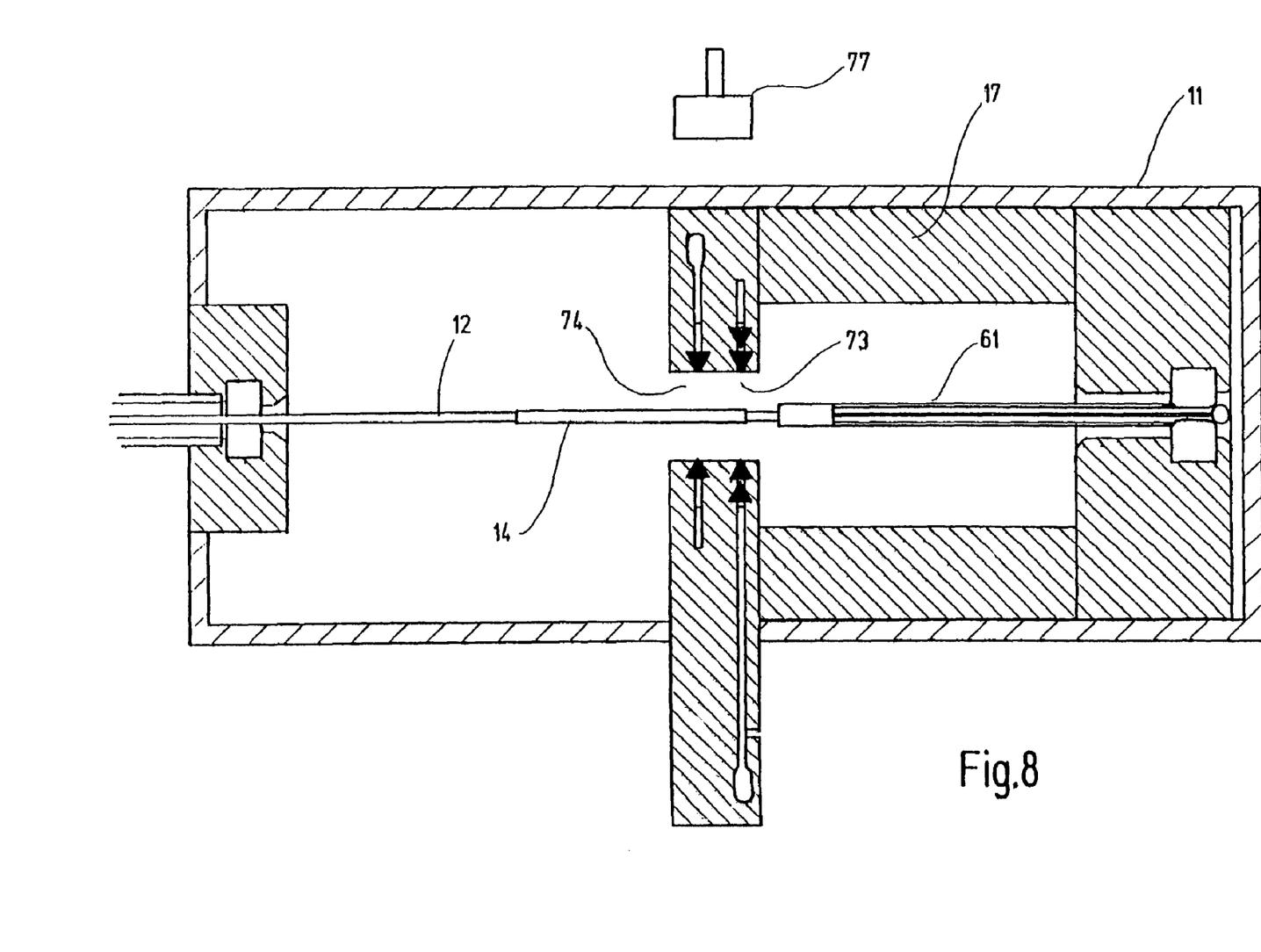
FIG. 8 shows a view as in FIG. 6, the spray carriage being in the position when coating has ended.

FIG. 8 shows the position of the spray carriage 17 in which the stent 14 has been completely coated. The protective sleeve 61 has now been removed completely from the stent 14, which is now finally dried by the compressed air emerging from the second annular nozzle 74. This position of the spray carriage 17 is detected by a second sensor 77 which is likewise provided on the base station 10.

Figure 9:
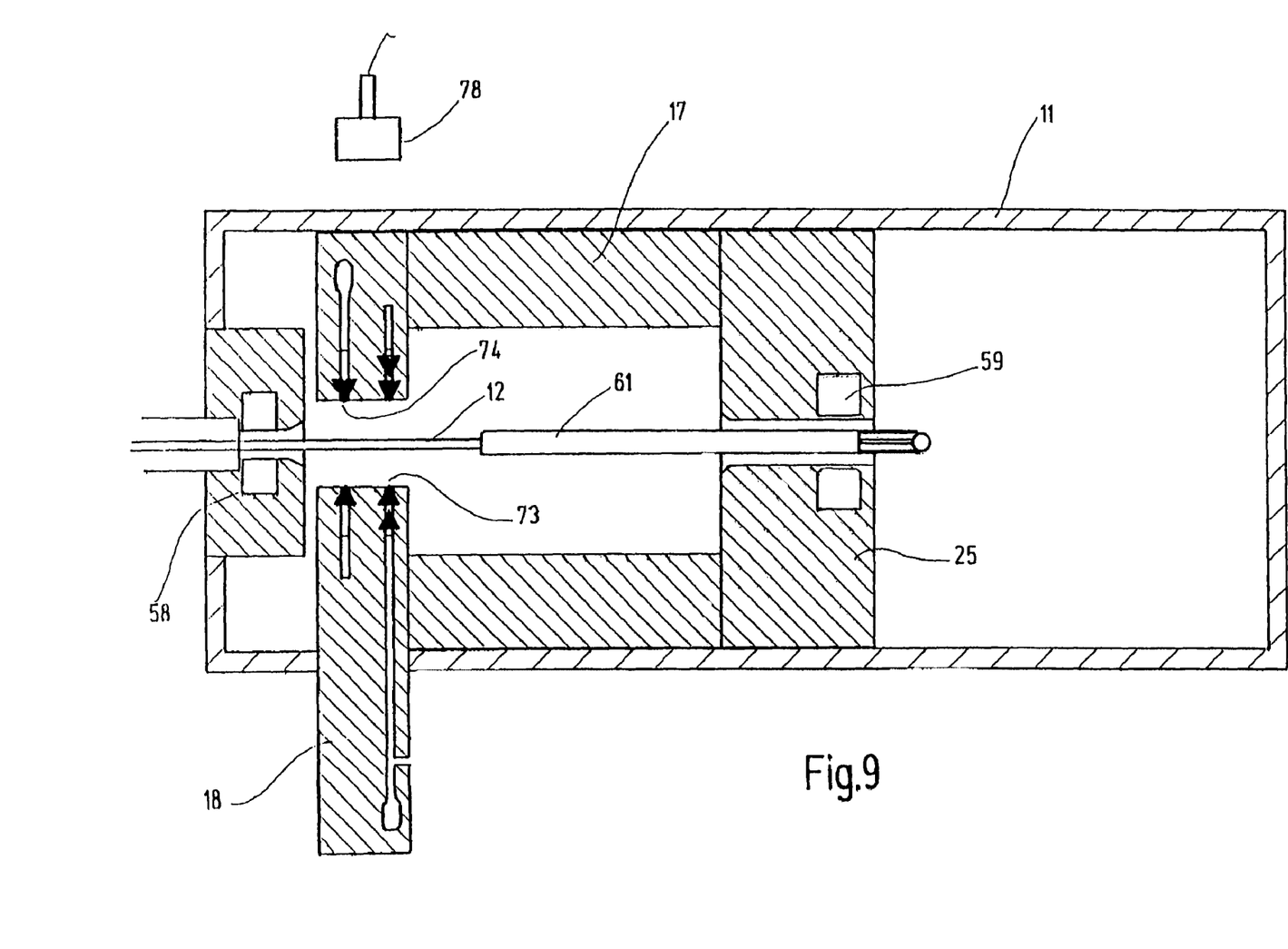
FIG. 9 shows a view as in FIG. 6, the spray carriage now being in the position for catheter removal.

After the drying procedure has ended, the spray carriage 17 is moved to the left in FIG. 8 until it reaches the position shown in FIG. 9, in which the catheter 12 can be removed. This position lies to the left of the start position shown in FIG. 6 and is detected by a third sensor, indicated at 78, which is likewise provided on the base station. When the spray carriage 17 has assumed the position shown in FIG. 9, the second clamp unit 59, as has already been discussed in connection with FIG. 5, was first opened via the wedge 68 as soon as the protective sleeve 61 was pushed back completely over the stent 14. Upon further movement of the spray carriage 17 to the left in FIG. 9, the first clamp unit 58 was then opened via the front ends 66 so that the catheter 12 with protective sleeve 61 can now be pulled leftwards from the cartridge 11. The cartridge 11 is then disposed of.

It should also be noted that the sensors 76, 77 and 78 are indicated in FIG. 1 by small boxes sitting on the window 33 on the support plate 32. It can be seen that the sequence in the longitudinal direction 37 is firstly sensor 78 (catheter removal position), then sensor 76 (start position) and, finally, sensor 77 (position when coating completed).

Figure 6:
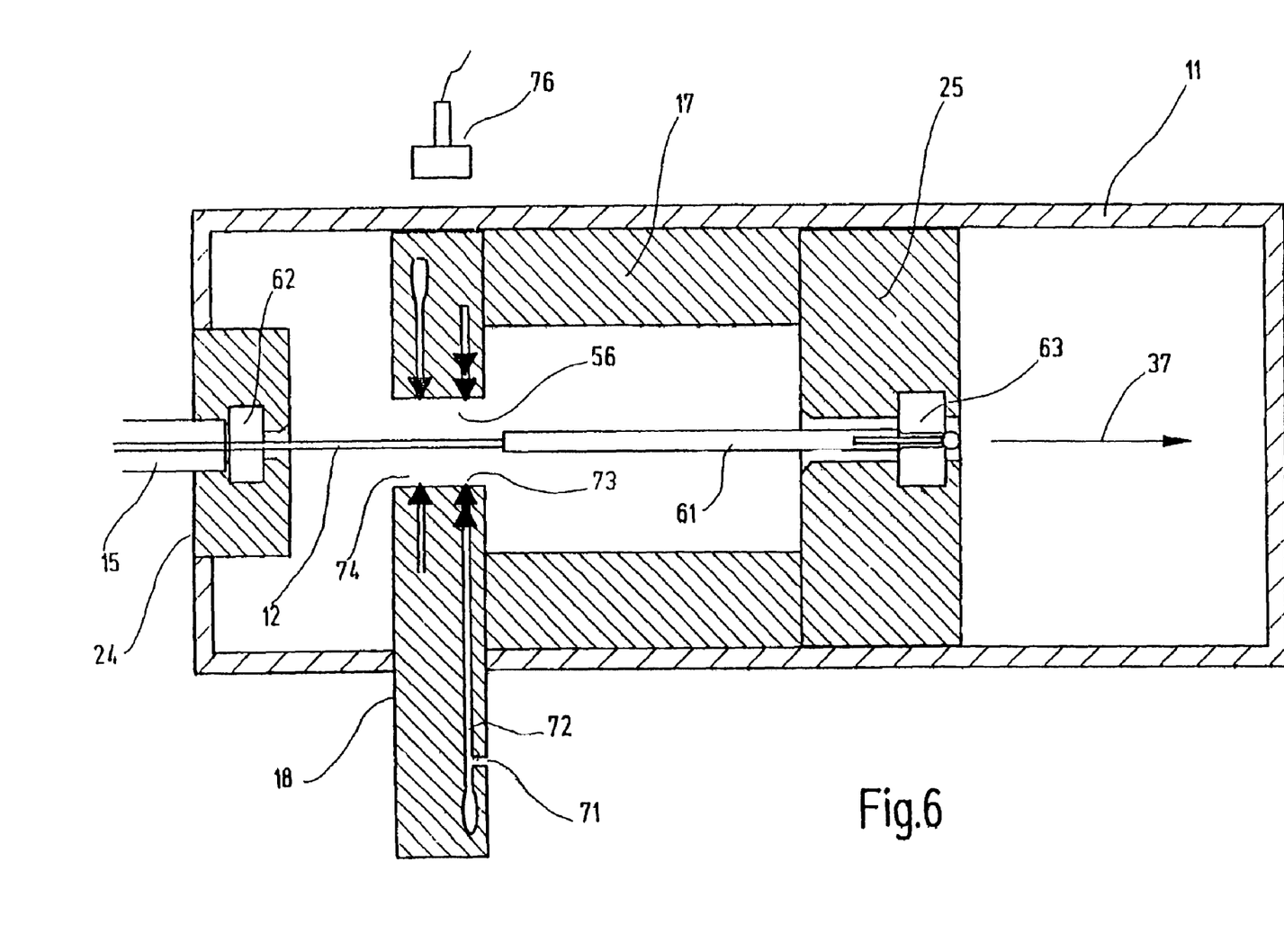
FIG. 6 shows a sectional plan view of the cartridge from FIG. 2, in the start position.
Figure 10:
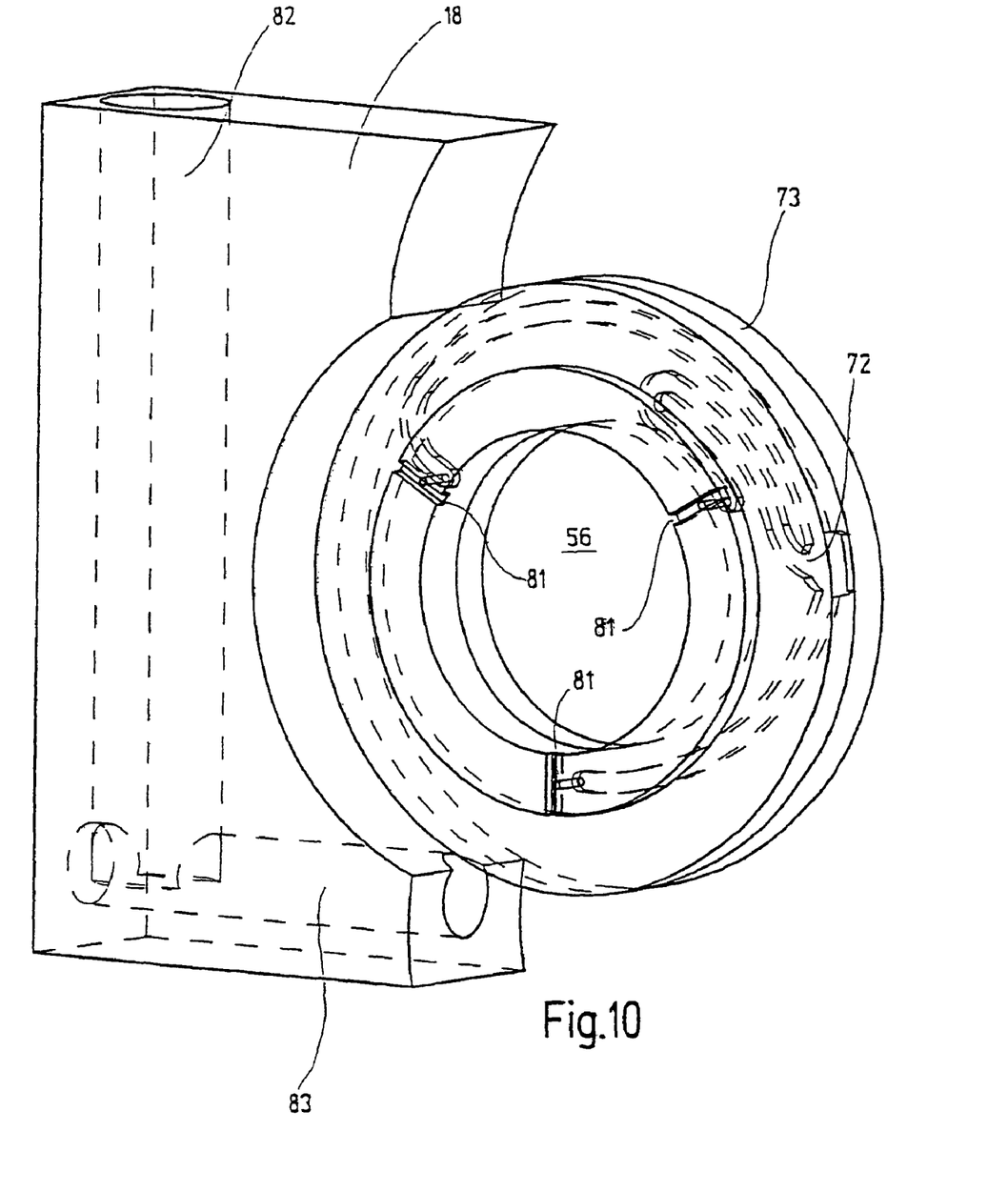
FIG. 10 shows a perspective view of the first annular nozzle used in the cartridge from FIG. 2.

Finally, FIG. 10 shows a perspective view of the first annular nozzle 73 which is clamped in the first wall 18. The first annular nozzle 73 is a disc-shaped plate with the through-hole 56 into which spray nozzles 81 open which, via the channel 72 already known from FIG. 6, are in fluid communication with the channel 71 and, via the latter, with the syringe 21. The active substance 22 is distributed through the channels 71 and 72 to the three spray nozzles 81 which open out symmetrically in the through-hole 56 and thus symmetrically surround the catheter 12 and stent 14.

For the sake of clarity, the first annular nozzle 74, designed in a similar way, is not shown in FIG. 10.

The second annular nozzle is supplied with compressed air via channels 82 and 83, the channel 83 leading to a similar inner channel system and to similar compressed air nozzles as is indicated by the channels 72 and the spray nozzles 81 for the first annular nozzle 73.

The second annular nozzle is connected via the channel 82 to the sterile filters 27 and 28.

The second annular nozzle 74 also symmetrically surrounds the implant to be coated, so that medicament deposited on the surface of the latter is dried uniformly.

The invention claimed is:

1. Device for applying active substances onto surfaces of medical implants, comprising a holder for the implants, an arrangement for applying the active substance onto the surface, a drive unit for moving the holder and the arrangement relative to one another, a base station and an exchangeable cartridge which can be mounted on the base station, wherein the drive unit is provided on the base station, and the holder and arrangement are provided on the cartridge, and wherein the cartridge comprises a carriage which is mounted so that it can move in a longitudinal direction and which is in engagement with the drive unit when the cartridge is mounted on the base station.

2. Device according to claim 1, wherein the cartridge has a carriage is a spray carriage.

3. Device according to claim 1, wherein the arrangement comprises a nozzle for spraying the active substance onto the surface, the arrangement being provided on the spray carriage.

4. Device according to claim 3, wherein the nozzle is a first annular nozzle which surrounds the circumference of an implant mounted in the cartridge.

5. Device according to claim 4, wherein the first annular nozzle is formed on a first wall of the spray carriage extending transversely with respect to the longitudinal direction, by channels which are distributed symmetrically in a circumferential arrangement and end in a through-hole which surrounds the mounted implant and is provided in the first wall.

6. Device according to claim 3, wherein an active substance reservoir in fluid communication with the first annular nozzle is provided on the spray carriage, on the first wall of the latter.

7. Device according to claim 3, wherein a plug connection in fluid communication with the first annular nozzle is provided on the spray carriage, on the first wall of the latter, said plug connection being provided for an exchangeable syringe which holds the active substance.

8. Device according to claim 7, wherein a limit stop for a piston of the syringe is provided on the base station.

9. Device according to claim 7, wherein the base station is provided with a first sensor which indicates when the spray carriage is situated in a start position in which the syringe can be mounted or exchanged.

10. Device according to claim 7, wherein the base station is provided with a second sensor which indicates when the spray carriage is situated in its end position in which the syringe is emptied.

11. Device according to claim 1, wherein the cartridge is provided with a second nozzle which, via the base station is in fluid communication with a reservoir for a drying agent.

12. Device according to claim 11, wherein the second nozzle is a second annular nozzle which is formed on a first wall of the spray carriage extending transversely with respect to the longitudinal direction, by channels which are distributed symmetrically in a circumferential arrangement and end in a through-hole which surrounds the mounted implant and is provided in the first wall.

13. Device according to claim 12, wherein, seen in the longitudinal direction, the second annular nozzle is arranged behind the first annular nozzle on the first wall.

14. Device according to claim 1, wherein, between base station and cartridge, at least one sterile filter is provided via which a drying agent can be conveyed into the cartridge when said cartridge is mounted on the base station.

15. Device according to claim 14, wherein the sterile filter is connected to a second nozzle.

16. Device according to claim 15, wherein the sterile filter is connected at its first end to the spray carriage and, with the cartridge mounted on the base station, is connected at its second end to the transport carriage.

17. Device according to claim 16, wherein two sterile filters are provided which are connected at their first end to the spray carriage and, with the cartridge mounted on the base station, are connected at their second end to the transport carriage.

18. Device according to claim 17, wherein the cartridge is closed off from the outside, and at least one further sterile filter is provided on the cartridge, via which further sterile filter the cartridge is in fluid communication with its environment.

19. Device according to claim 1, wherein a transport carriage which can be moved via the drive unit is provided on base station, said transport carriage being connected to the spray carriage when the cartridge is mounted on the base station.

20. Device according to claim 1, wherein the cartridge has, at its end face, a first clamp unit as a holder for the implants.

21. Device according to claim 1, wherein the implants are stents.

22. Device for applying active substances onto surfaces of medical implants, comprising a holder for the implants, an arrangement for applying the active substance onto the surface, a drive unit for moving the holder and the arrangement relative to one another, a base station and an exchangeable cartridge which can be mounted on the latter, wherein the drive unit is provided on the base station, and the holder and arrangement are provided on the cartridge, and wherein the cartridge is provided with a second clamp unit as a holder for a protective sleeve surrounding the implants, said second clamp unit being able to move relative to the implant in the longitudinal direction in order to remove the protective sleeve from the implant.

23. Device according to claim 22, wherein the second clamp unit is formed on the spray carriage, said second clamp unit being formed at a second wall of the spray carriage remote from the end face, and the first and second walls further having a distance from one another, in the longitudinal direction, which is greater than the implant in its longitudinal extent.

24. Device according to claim 23, wherein the first clamp unit is designed to receive a catheter carrying a stent, and the second clamp unit is designed to receive a protective sleeve fitting over the stent.

25. Device according to claim 22, wherein each an unlocking arrangement is provided for the first and second clamp units, which unlocking arrangement automatically re-leases the implant when the spray carriage is moved past its start position, adopted upon mounting of the implant, towards the first end face.

26. Device according to claim 25, wherein the unlocking arrangement for the first clamp unit is arranged between the first end face and the unlocking arrangement for the second clamp arrangement.

27. Device according to claim 25, wherein the base station is provided with a third sensor which indicates when the spray carriage is situated in a removal position, in which the first and second clamp units are unlocked, so that the implant can be re-moved.

28. Device according to claim 22, wherein the implants are stents.

* * * * *